US 6,417,513 B1

(12) United States Patent
Hershey et al.

(10) Patent No.: US 6,417,513 B1
(45) Date of Patent: Jul. 9, 2002

(54) METHOD AND APPARATUS FOR DETECTING A CHANGE IN WATER VAPOR ABOVE A COOKTOP SURFACE

(75) Inventors: John Erik Hershey, Ballston Lake; Ertugrul Berkcan, Clifton Park, both of NY (US)

(73) Assignee: General Electric Company, Schenectady, NY (US)

( * ) Notice: Subject to any disclaimer, the term of this patent is extended or adjusted under 35 U.S.C. 154(b) by 15 days.

(21) Appl. No.: 09/749,847

(22) Filed: Dec. 28, 2000

(51) Int. Cl.[7] .............................................. G01N 21/35
(52) U.S. Cl. ..................................................... 250/338.5
(58) Field of Search ....................................... 250/338.5

(56) References Cited

U.S. PATENT DOCUMENTS

| | | | | |
|---|---|---|---|---|
| 5,493,119 A | * | 2/1996 | Torngren | 219/707 |
| 5,923,035 A | * | 7/1999 | Winkler et al. | 250/338.5 |
| 6,140,617 A | * | 10/2000 | Berkcan et al. | 219/446.1 |

* cited by examiner

*Primary Examiner*—Constantine Hannaher
(74) *Attorney, Agent, or Firm*—John F. Thompson; Jill M. Breedlove

(57) ABSTRACT

An apparatus detects changes in water vapor above a cooktop surface and includes a radiation source that is positioned below the cooktop surface. The radiation source emits radiation having a predetermined water vapor absorption wavelength. A beam splitter splits the emitted radiation into a first radiation beam and a second radiation beam. The first radiation beam is directed through and above the cooktop surface. A reflective surface positioned above the cooktop surface reflects the first radiation beam. A radiation sensor detects the reflected first radiation beam and generates a sensor output. A reference radiation sensor receives the second radiation beam from the beam splitter and generates a reference output. A processor is connected to the radiation sensor and the reference radiation sensor and receives the sensor output and the reference output. Changes in water vapor above the cooktop surface are determined by analyzing the sensor output and the reference output.

47 Claims, 2 Drawing Sheets

METHOD AND APPARATUS FOR DETECTING A CHANGE IN WATER VAPOR ABOVE A COOKTOP SURFACE

BACKGROUND OF THE INVENTION

The present invention relates to a method and apparatus for detecting a change in water vapor above a cooktop surface, and more particularly, to a method and apparatus for detecting a change in water vapor above a cooktop surface by analyzing the water absorption of a predetermined wavelength of radiation directed above the cooktop surface.

Boiling water, other liquids or foods, collectively referred to herein as liquids, is one of the most common uses for a cooktop and/or range. It is typically desirable to closely monitor the boil phase and/or state of the liquid during the cooking process. The boil phase and/or state is monitored for a number of reasons. First, many cooking processes require that the liquid be attended to upon identification of a particular boil phase and/or state, such as, for example, stirring or adding ingredients. In addition, the boil phase and/or state may be monitored to reduce heat after the liquid reaches a boil, such as, for example, to reduce the liquid to a simmer or to prevent boil-over. Boil-over can result in a burned-on mess or, in the case of a gas powered heat source, the cooking flame can become extinguished. Moreover, a liquid not monitored upon boiling can boil dry which can result in the burning of the food, damage to vessels or other detrimental situations. Conventionally, the boil phase and/or state is monitored visually. Such visual monitoring can interfere with the ability of a user to prepare other foods or be otherwise fully productively disposed during heating of the liquid. Moreover, a busy or inexperienced user may fail to accurately identify a boil phase and/or state of interest in a timely manner.

For cooktops and ranges having energy sources using electric, inductive or gas power, the determination of the boil phases and/or states of a liquid being heated on the cooktop and/or range has traditionally focused on temperature monitoring or sensing. Various temperature sensors have been proposed for sensing the temperature of a surface heating source, a cooking vessel positioned on a cooktop surface or the contents of the vessel positioned on the cooktop. These temperature sensors can also be used to control the energy supplied to the heating source based upon the sensed temperature. In particular, such sensors have commonly been proposed for use in connection with glass-ceramic cooktops and/or ranges. Temperature-based sensing systems can indirectly or inferentially provide information regarding a boil phase and/or state of a liquid contained in a vessel being heated on the cooktop surface. However, some temperature-based sensing systems may not reliably determine the boil phase and/or state. This unreliability is partially based on the fact that the correlation between temperature and boil phase and/or state depends on a number of variables, such as, for example, the type of liquid, the amount of liquid, any additives, the position of the vessel and the physical characteristics of the vessel.

In addition, some conventional cooktops and/or ranges identify the boil phases and/or states of a liquid by analyzing acoustic emissions produced by the liquid during heating. Various signal processing circuits and other processors are implemented to analyze the acoustic emission and determine the boil phases and/or states of the liquid. However, these acoustic sensing systems also are dependent upon a number of variables, such as, for example, the position of the vessel and the physical characteristics of the vessel.

The boil phases and/or states that the liquid passes through during heating can be identified by scientific names which characterize the physical changes of the heated liquid. The term "convection" may be used to describe a pre-simmer phase in which the initial heating of the liquid from ambient to a temperature approaching the boiling point occurs. "Pop-corn" or a "ping" is a term that may be used for a simmer onset phase in which the first signs of coalescence of nucleation of gases dissolved in the liquid and gases produced by the heating appear at sites within the vessel, for example, at surface irregularities along the bottom and side walls of the vessel, and such gas bubbles begin to travel towards the surface of the liquid to escape. These bubbles collapse when leaving the hotter inner surface of the vessel. "Jet" nucleation occurs in a simmer phase, in which gas bubbles are formed more frequently and are of larger size, and in which the bubbles also more rapidly rise to the upper surface of the liquid to escape. The boil phase may also be termed "rolling boil", and at this stage, the liquid is highly agitated by the increased number of gas bubbles formed causing water vapor to escape from the liquid. The vaporizing of the water in the vessel increases the amount of water vapor, also termed humidity, above the vessel and the cooktop surface. Therefore, each of the boil phases and/or states is characterized by an increase in water vapor above the cooktop surface. Thus, it would be desirable to have a system and method that detects a change in the water vapor above the cooktop surface as a way to determine the boil phase and/or state of the liquid being heated.

BRIEF SUMMARY OF THE INVENTION

In one representative embodiment, an apparatus for detecting a change in water vapor above a cooktop surface is provided. The apparatus comprises a radiation source that is positioned below the cooktop surface. The radiation source generates and emits radiation. The emitted radiation has at least a predetermined water vapor absorption wavelength. In one embodiment, the radiation source emits the radiation at a predetermined reflectance angle to the cooktop surface such that the emitted radiation is split into a first radiation beam and a second radiation beam. In another embodiment, the radiation source emits the radiation to a beam splitter that splits the emitted radiation into a first radiation beam and a second radiation beam. The first radiation beam is directed through and above the cooktop surface. The second radiation beam comprises reference radiation. A reflective surface is positioned above the cooktop surface and reflects the first radiation beam toward the cooktop surface. A radiation sensor is positioned below the cooktop surface and detects the reflected first radiation beam. The radiation sensor generates a sensor output that corresponds to the reflected radiation beam. A reference radiation sensor is positioned below the cooktop surface and receives the second radiation beam. The reference radiation sensor generates a reference output corresponding to the second radiation beam. A processor is connected to the radiation sensor and the reference radiation sensor, the processor receiving the sensor output and the reference output and determining a change in water vapor above the cooktop surface by analyzing the sensor output and the reference output.

In another representative embodiment, a method for detecting a change in water vapor above a cooktop surface is provided. The method comprises the steps of generating radiation at a position below the cooktop surface. The generated radiation has at least a predetermined water absorption wavelength. In one embodiment, the generated radiation is emitted to a beam splitter. In another embodiment, the generated radiation is emitted at a predetermined reflectance angle with respect to the cooktop surface. The radiation is split into at least a first radiation beam and a second radiation beam. The first radiation beam is directed through the cooktop surface to a position above the cooktop surface. In addition, the first radiation beam is reflected toward the cooktop surface using a reflective surface. The reflected first radiation beam passes through the cooktop surface, and the reflected first radiation beam is detected using a radiation sensor that is positioned below the cooktop surface. The radiation sensor generates a sensor output. The sensor output corresponds to the reflected first radiation beam. The second radiation beam is directed toward a reference sensor. Also, the second radiation beam is detected using the reference sensor. The reference sensor generates a reference output that corresponds to the second radiation beam. The sensor output and the reference output are analyzed at the predetermined water absorption wavelength of the generated radiation. A change in water vapor above the cooktop surface is determined from the analysis.

DETAILED DESCRIPTION OF THE INVENTION

Figure 1:
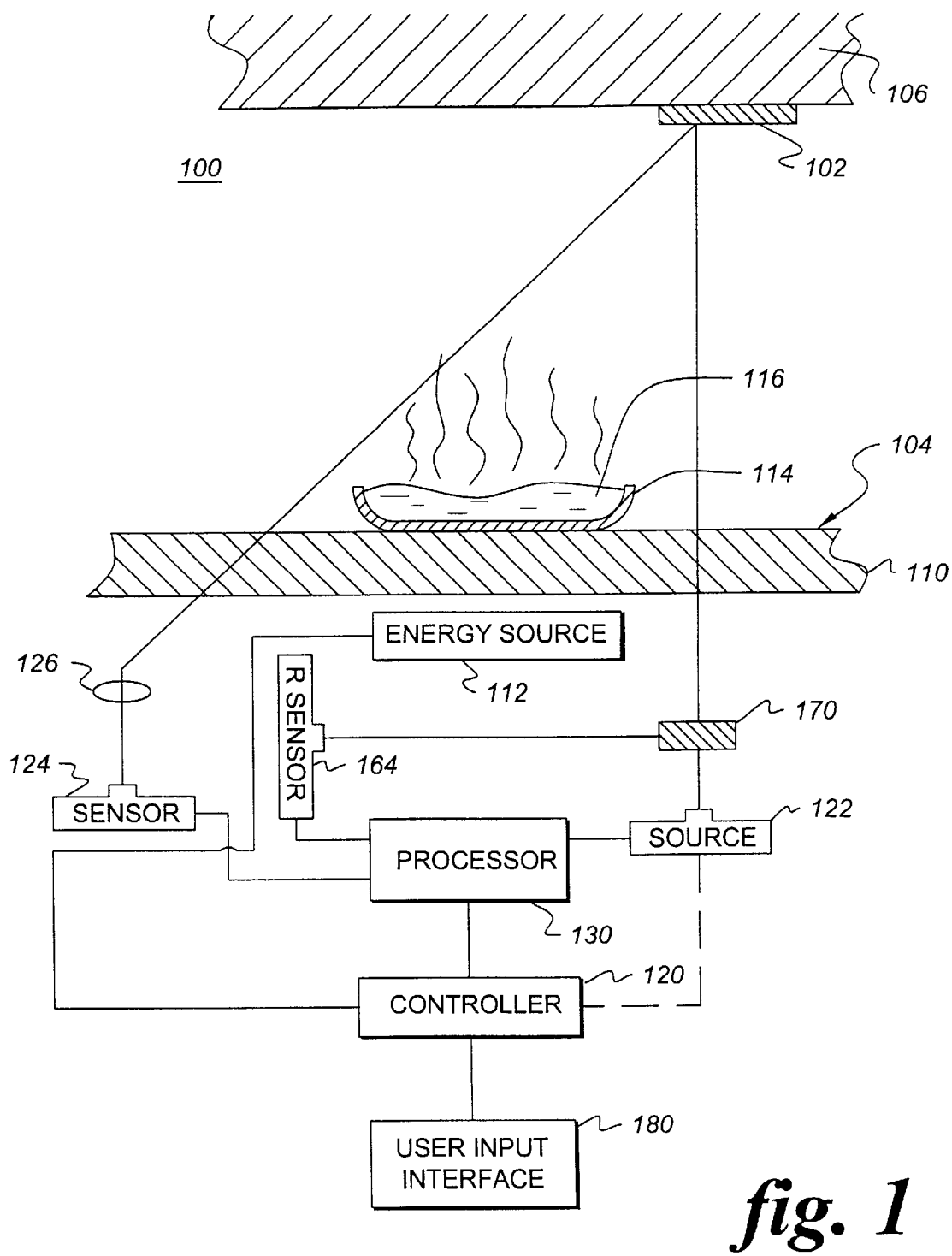
FIG. 1 is a cross-sectional and block diagram view of one representative embodiment of a cooktop.
Figure 2:
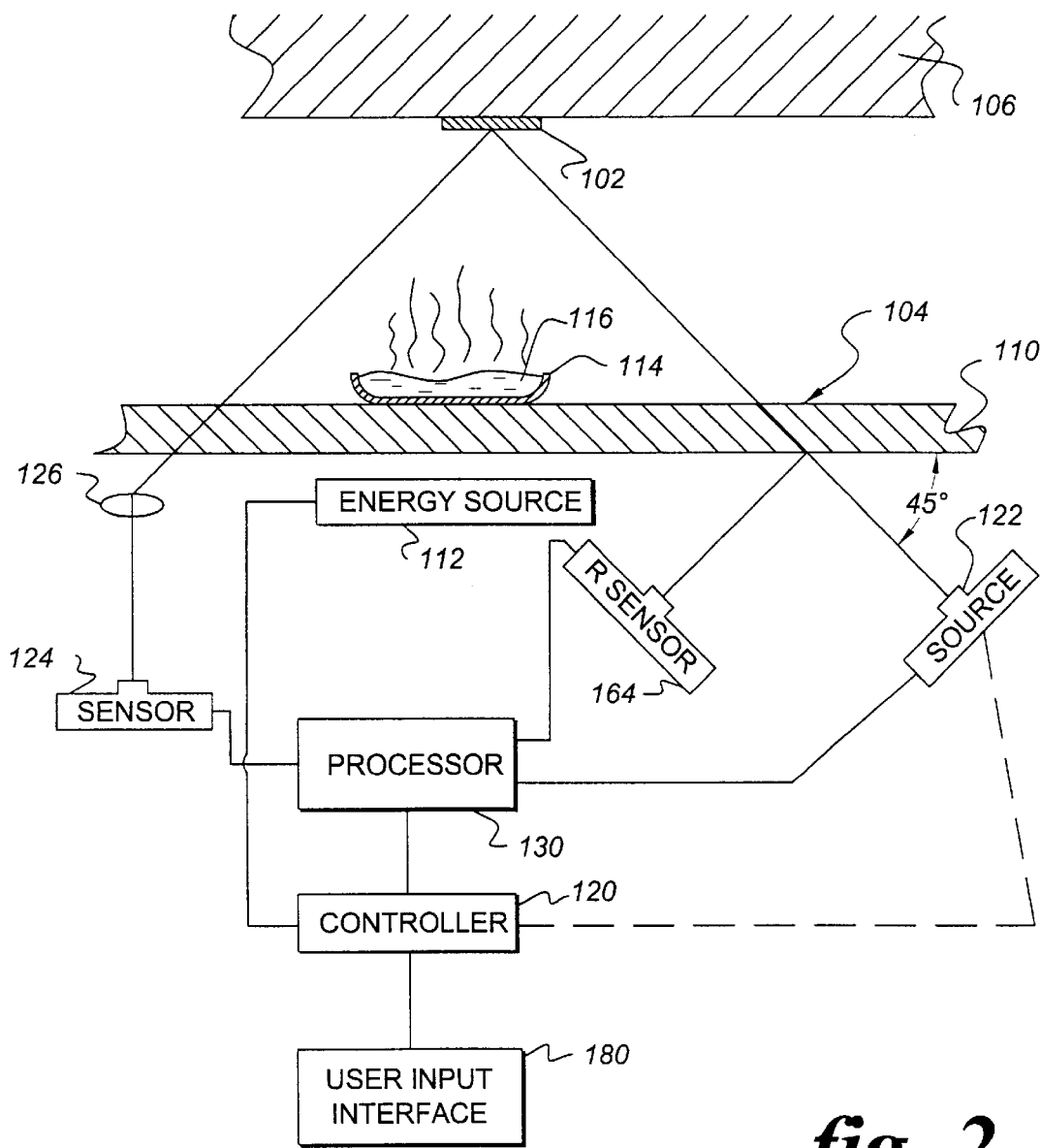
FIG. 2 is a cross-sectional and block diagram view of another representative embodiment of a cooktop.

In FIGS. 1 and 2, a monitoring and control system 100 includes a cooktop 104 comprising a cooktop surface 110 positioned below a reflective surface 102. The cooktop surface 110 can be composed of, for example, any suitable solid material, such as glass-ceramic. The reflective surface 102 can, in one embodiment, be composed of any reflective material, such as, for example, a mirror or brightly polished surface that is attached to a ceiling or range hood 106. In another embodiment, the reflective surface 102 can be any surface that reflects radiation, such as, for example, a ceiling or range hood 106. In one embodiment, an energy source 112 is positioned below the cooktop surface 110. The energy source 112 can comprise, for example, any suitable energy source, such as electric or gas heating elements and/or induction heating sources. A user can selectively place a vessel 114, such as a pot and/or pan, on the cooktop 110. The vessel 114 contains contents 116 that can be heated by the energy source 112. A controller 120 is connected to the energy source 112 and controls the amount of heat produced by the energy source 112. A user can control the amount of energy supplied to the energy source 112 via user input interface 180.

Also shown in FIGS. 1 and 2, a radiation source 122 can, in one embodiment, be connected to a processor 130. The radiation source 122 generates and emits radiation. In one embodiment, the processor 130 controls the generation and emission of radiation from the radiation source 122. In another embodiment, the radiation source 122 constantly generates and emits radiation without being connected to or controlled by the processor 130. In even another embodiment, the radiation source 122 is connected to the controller 120 that controls the generation and emission of the radiation from the radiation source 122. In one embodiment, the radiation source 122 comprises a broadband incoherent light source having a suitable optical filter to produce the desired radiation.

In one embodiment, the radiation generated and emitted by the radiation source 122 comprises at least one wavelength that has water absorption characteristics. In this regard, the radiation source 122 can emit more than one wavelength of radiation and among the wavelengths is at least one water absorption wavelength. The water absorption wavelength is a wavelength line that has a water absorption coefficient, also termed water absorption level. As such, comparing a reference water absorption level to a water absorption level of the radiation line that passes near a water vapor source allows the determination of at least a change in the water vapor from the water vapor source. It should also be appreciated that, in another embodiment, the radiation generated and emitted by the radiation source 122 comprises a laser line that does not correspond to an absorption wavelength.

In one embodiment, the radiation source 122 comprises a laser. In another embodiment, the radiation source 122 comprises an indium gallium arsenide phosphorus (InGaAsP) laser. In even another embodiment, the radiation generated and emitted by the InGaAsP laser comprises at least a wavelength of 1.393 microns ($\mu$m) which has water absorption characteristics. The radiation can comprise several wavelength ranges, such as, for example, about 0.94 microns ($\mu$m) to about 1.396 microns ($\mu$m); about 0.94 microns ($\mu$m) to about 2.7 microns ($\mu$m); about 0.94 microns ($\mu$m) to about 1.06 microns ($\mu$m); about 0.94 microns ($\mu$m) to about 1.1 microns ($\mu$m); about 1.06 microns ($\mu$m) to about 1.3 microns ($\mu$m); about 1.1 microns ($\mu$m) to about 1.38 microns ($\mu$m); about 1.3 microns ($\mu$m) to about 1.38 microns ($\mu$m); about 1.3 microns ($\mu$m) to about 1.396 microns ($\mu$m); about 1.38 microns ($\mu$m) to about 1.87 microns ($\mu$m) and about 1.87 microns ($\mu$m) to about 2.7 microns ($\mu$m). It should be appreciated, as discussed herein, that the radiation emitted from the radiation source 122 has, in one embodiment, a wavelength that has water absorption characteristics. It should also be appreciated that having a wavelength with water absorption characteristics also encompasses emitted radiation that has one or more wavelength ranges with water absorption characteristics. In yet another embodiment, the wavelength of the radiation emitted by the radiation source 122 can comprise at least one of the wavelengths and/or wavelength lines or the range between any two of the wavelengths or wavelength lines of Table 1.

TABLE 1

| Laser Line ($\mu$m) | Water Absorption Wavelength ($\mu$m) |
| --- | --- |
| 0.94 | 0.94 |
| 1.06 | 1.1 |
| 1.3 | 1.38 |
| 1.396 | 1.87 |
| | 2.7 |

As shown in FIGS. 1 and 2, in one embodiment, the radiation source 122 can be positioned below the cooktop surface 110 and emit radiation through the cooktop surface 110 toward a reflective surface 102. In another embodiment, the radiation source 122 can be positioned above or flush with the cooktop surface 110 to emit radiation directly toward the cooktop surface 110 and/or toward the reflective surface 102. Also shown in FIG. 1, in one embodiment, a beam splitter 170 can be connected to or positioned proximate to the radiation source 122 to split the radiation emitted from the radiation source 122. The beam splitter 170 provides at least two radiation beams where a first radiation beam is directed toward the reflective surface 102 and/or the cooktop surface 110 and a second radiation beam comprises reference radiation. The second radiation beam is directed toward a reference sensor 164. In one embodiment, the reference sensor 164 comprises a germanium-type detector. The reference sensor 164 senses the second radiation beam (reference radiation) and produces a reference output that corresponds to the second radiation beam (reference radiation). In one embodiment, the reference output can be used by the processor 130 to determine at least one boil phase and/or state of the contents 116 of the vessel 114. It should be appreciated that, in one embodiment, the second radiation beam (reference radiation) can supply a base line water absorption level. It should also be appreciated that, in another embodiment, the second radiation beam (reference radiation) comprises a known water absorption level. In one embodiment, the reference output is used to obtain a baseline for the level of the radiation emitted by the radiation source 122. This level is then used by the processor 130 to compare the radiation detected by the radiation sensor 124 and to determine the at least one boil phase and/or state.

In FIG. 2, the radiation source 122 generates and emits radiation toward the cooktop surface 110 at a reflectance angle. In one embodiment, the reflectance angle is an acute angle with respect to the cooktop surface 110. In another embodiment, the reflectance angle comprises about forty-five degrees (45°) with respect to the cooktop surface 110. When the radiation is emitted at the reflectance angle, at least a first radiation beam and a second radiation beam are created. In one embodiment, the first radiation beam is emitted through the cooktop surface 110 and toward the reflective surface 102. In addition, the second radiation beam can comprise reference radiation. In one embodiment, as shown in FIG. 2, the second radiation beam is reflected by the cooktop surface 110 toward a reference sensor 164. The reference sensor 164 can comprise, in one embodiment, a germanium-type detector. In addition, the reference sensor 164 senses the second radiation beam (reference radiation) and produces a reference output that corresponds to the second radiation beam (reference radiation). In one embodiment, the reference output can be used by the processor 130 to determine at least one boil phase and/or of the contents 116 of the vessel 114. It should be appreciated that, in one embodiment, the second radiation beam (reference radiation) can supply a base line water absorption level. It should also be appreciated that, in another embodiment, the second radiation beam (reference radiation) comprises a known water absorption level.

A radiation sensor 124 is positioned below the cooktop surface 110 and senses radiation that passes through the cooktop surface 110. The sensed radiation can be emitted from the radiation source 122. In another embodiment, the radiation sensor 124 comprises a germanium-type detector. The radiation sensor 124 generates a sensor output that corresponds to the radiation sensed by the radiation sensor 124. In one embodiment, the radiation sensed by the radiation sensor 124 relates to at least one boil phase and/or state of the contents 116 of the vessel 114. The radiation sensor 124 is connected to the processor 130. In one embodiment, the processor 130 uses the sensor output to determine at least one boil phase and/or state of the contents 116 of the vessel 114. In another embodiment, the processor 130 includes a signal conditioner (not shown) that can be used to amplify and/or condition the sensor output from the radiation sensor 124 and/or the reference output from the reference sensor 164.

In one embodiment, the radiation sensor 124 and/or the reference sensor 164 can be temperature compensated. Temperature compensation can be accomplished using a signal relating to the ambient temperature around the radiation sensor 124 and/or the reference sensor 164. For example, a temperature sensor (not shown), such as a thermistor, can be used to measure the temperature of the radiation sensor 124 and/or the reference sensor 164 and which, in one embodiment, is connected to software programs in processor 130 using separate channels of an A/D converter (not shown). Alternatively, in another embodiment, temperature compensation is accomplished using a separate hardware implementation.

In even another embodiment, the radiation sensor 124 and/or the reference sensor 164 can comprise, for example, a thermal detector, a photon detector or a quantum detector or other detectors/sensors that detect or sense infrared radiation (i.e., broadband sensors). In embodiments where the radiation sensor 124 and/or the reference sensor 164 comprises a thermal detector, these detectors have a responsive element that is sensitive to temperature resulting from the incident radiation, and an exemplary thermal detector can comprise, for example, a thermopile or a bolometric detector. In other embodiments where the radiation sensor 124 and/or the reference sensor 164 comprises a quantum detector or photon detector, these detectors have a responsive element that is sensitive to the number or mobility of free charge carriers, such as electrons and holes, due to the incident infrared photons. For example, a photon detector can comprise types, such as, silicon-type, germanium-type, and indium gallium arsenide (InGaAs) type. In even another embodiment, the radiation sensor 124 and/or the reference sensor 164 can comprise a plurality of detectors comprising at least one relatively narrow band quantum detector, such as a silicon or germanium photo-diode. In these embodiments, the plurality of detectors can be used to separate the wavelength sensitivity and increase the specificity and sensitivity of the radiation sensor 124 and/or reference sensor 164. In addition, the plurality of detectors may comprise detectors that detect different (e.g., two) ranges of wavelength.

As shown in FIGS. 1 and 2, a wide field of view lens 126 is attached to or positioned proximate to the radiation sensor 124 such that the field of view of the radiation sensor 124 is increased. The portion of the cooktop surface 110 that contributes to the radiation collected by the radiation sensor 124 or that can be "seen" by the radiation sensor 124 is termed the field of view. The radiation sensor 124 receives at least a portion of radiation reflected from the reflective surface 102 that passes through the cooktop surface 110. The radiation within the field of view is sensed by radiation sensor 124 and the radiation sensor 124 produces a sensor output in response to the sensed radiation. In another embodiment, a radiation collector (not shown), such as, for example, a conventional parabolic light concentrator (i.e., a paraboloid of revolution) or a compound parabolic light concentrator, is used to increase the field of view of the radiation sensor 124. In one embodiment, the radiation collector (not shown) is attached to or positioned proximate to the radiation sensor 124, and the radiation collector (not shown) is used such that the radiation, reflected from the reflective surface 102, is collected and guided toward the radiation sensor 124.

In one representative embodiment of operation, the radiation source 122 generates radiation at a position below the cooktop surface 110. The radiation generated by the radiation source 122 comprises at least a predetermined water absorption wavelength. The radiation is emitted toward the cooktop surface 110. In one embodiment, the radiation is emitted to a beam splitter 170 that splits the radiation into at least a first radiation beam and a second radiation beam. In another embodiment, the radiation is emitted toward the cooktop surface 110 at a predetermined reflectance angle with respect to the cooktop surface 110. The emission of the radiation at the reflectance angle produces at least a first radiation beam and a second radiation beam. In one embodiment, the reflectance angle is an acute angle relative to the cooktop surface 110. In another embodiment, the reflectance angle comprises about forty-five degrees (45°).

The first radiation beam is directed through the cooktop surface 110 to a position above the cooktop surface 110. In addition, the first radiation beam is reflected back toward the cooktop surface 110 by a reflective surface 102. In one embodiment, the reflected first radiation beam is directed near an area above the vessel 114 where the water absorption level of the first reflected radiation beam reflects the water vapor level, i.e. humidity, above the vessel 114. The reflected first radiation beam is directed though the cooktop surface 110. The radiation sensor 124 senses the reflected first radiation beam and a sensor output is generated that corresponds to the reflected first radiation beam. The second radiation beam comprises reference radiation. In addition, the second radiation beam is directed toward a reference sensor 164 that senses the second radiation beam. The reference sensor 164 generates a reference output in response to the second radiation beam (reference radiation).

The sensor output and the reference output are analyzed at the predetermined water absorption wavelength. In one embodiment, the analysis comprises comparing the sensor output to the reference output. In another embodiment, the analysis comprises analyzing the sensor output and the reference output at a predetermined wavelength to account for any variation of the intensity of the radiation source 122. In another embodiment, the analysis comprises determining, at the predetermined water absorption wavelength, a water absorption level of the reference signal (reference absorption) and a water absorption level of the reflected first radiation beam (reflected absorption). Then, by comparing the reference absorption to the reflected absorption, a change in the water absorption level can be determined. In addition, by comparing the reference absorption to the reflected absorption over a predetermined amount of time, at least one boil phase and/or state of the contents 116 of the vessel 114 can be determined. In one embodiment, the processor 130 performs the analysis via a program or software application stored in a memory location, such as, for example, dynamic/static memory or a magnetic media disk drive. In another embodiment, the analysis is performed by the controller 120 via, such as, for example, a program or software application stored in a memory location, such as, for example, dynamic/static memory or a magnetic media disk drive.

When the change between reference absorption and the reflected absorption is determined, at least one boil phase and/or state of the contents 116 of the vessel 114 can be determined. In one embodiment, the at least one boil phase and/or state can comprise a pre-simmer phase, a simmer onset phase, a simmer phase or a boil phase. In addition, the boil phase can also comprise a boil dry phase or a boil over phase. It should be appreciated that each boil phase and/or state can be characterized by a predetermined water absorption level, water vapor level and/or humidity above the vessel 114. In one embodiment, discrete water absorption levels of the reflected absorption can be determined, and these discrete water absorption levels can be compared to reference water absorption levels to determine the boil phase and/or state. The reference water absorption levels can comprise characterized predetermined water absorption levels that relate to and/or can be correlated to a predetermined boil phase and/or state. In addition, in another embodiment, the water absorption level can be determined over a predetermined amount of time to obtain a water absorption level curve. Once obtained, the water absorption level curve can be compared to a reference water absorption level curve such that the boil phases and/or states of the contents 116 of the vessel 114 are determined. The reference water absorption level curve can be programmed in the processor 130 and/or controller 120 during manufacturing or during installation of the cooktop 104.

The foregoing discussion of the invention has been presented for purposes of illustration and description. Further, the description is not intended to limit the invention to the form disclosed herein. Consequently, variations and modifications commensurate with the above teachings and with the skill and knowledge of the relevant art are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A method for detecting a change in water vapor above a cooktop surface, the method comprising the steps of:

providing radiation to a position above the cooktop surface, the provided radiation having a predetermined water vapor absorption wavelength;

reflecting the radiation toward the cooktop surface;

detecting the reflected radiation using a radiation sensor;

generating a sensor output from the radiation sensor, the sensor output corresponding to the reflected radiation;

providing reference radiation;

detecting the reference radiation using a reference sensor;

generating a reference output from the reference sensor, the reference output corresponding to the reference radiation;

analyzing the sensor output and the reference output; and determining a change in the water vapor above the cooktop surface from the step of analyzing.

2. The method of claim 1 wherein the step of providing radiation comprises emitting radiation from an InGaAsP laser and the step of providing reference radiation comprises emitting radiation from the InGaAsP laser.

3. The method of claim 1 further comprising the step of increasing a field of view of the radiation sensor using a lens.

4. The method of claim 1 further comprising the step of increasing a field of view of the radiation sensor using a radiation collector.

5. The method of claim 1 wherein the step of providing radiation comprises emitting a laser line having a wavelength selected from the group consisting of about 0.94 $\mu$m, about 1.06 $\mu$m, about 1.3 $\mu$m and about 1.396 $\mu$m.

6. The method of claim 1 wherein the step of providing radiation comprises emitting radiation having a wavelength range of about 0.94 $\mu$m to about 1.396 $\mu$m.

7. The method of claim 1 wherein the step of providing radiation comprises emitting radiation having a wavelength range of about 0.94 $\mu$m to about 2.7 $\mu$m.

8. The method of claim 1 wherein the step of providing reference radiation comprises splitting the radiation provided in the step of providing radiation into at least a first radiation beam and a second radiation beam wherein the first radiation beam is directed above the cooktop surface and the second radiation beam comprises the reference radiation.

9. The method of claim 1 wherein the step of analyzing the sensor output and the reference output comprises analyzing the sensor output and the reference output at a predetermined water absorption wavelength of the provided radiation.

10. The method of claim 1 wherein the step of analyzing the sensor output and the reference output comprises analyzing the sensor output and the reference output at a predetermined water absorption wavelength to account for a variation of the intensity of the radiation source.

11. The method of claim 1 wherein the step of determining a change in water vapor comprises continually comparing the sensor output to the reference output.

12. A method for detecting a change in water vapor above a cooktop surface, the method comprising the steps of:
generating radiation at a position below the cooktop surface, the generated radiation having a predetermined water absorption wavelength;
emitting the generated radiation to a beam splitter;
splitting the radiation into at least a first radiation beam and a second radiation beam;
directing the first radiation beam through the cooktop surface to a position above the cooktop surface;
reflecting the first radiation beam toward the cooktop surface using a reflective surface;
passing the reflected first radiation beam through the cooktop surface;
detecting the reflected first radiation beam using a radiation sensor positioned below the cooktop surface;
generating a sensor output from the radiation sensor, the sensor output corresponding to the reflected first radiation beam;
directing the second radiation beam toward a reference sensor;
detecting the second radiation beam using the reference sensor;
generating a reference output from the reference sensor, the reference output corresponding to the second radiation beam;
analyzing the sensor output and the reference output at the predetermined water absorption wavelength of the generated radiation; and
determining a change in water vapor above the cooktop surface from the step of analyzing.

13. The method of claim 12 wherein the step of generating radiation comprises generating radiation from an InGaAsP laser.

14. The method of claim 12 further comprising the step of increasing a field of view of the radiation sensor using a lens.

15. The method of claim 12 further comprising the step of increasing a field of view of the radiation sensor using a radiation collector.

16. The method of claim 12 wherein the step of generating radiation comprises generating a laser line having a wavelength selected from the group consisting of about 0.94 $\mu$m, about 1.06 $\mu$m, about 1.3 $\mu$m and about 1.396 $\mu$m.

17. The method of claim 16 wherein the step of emitting the generated radiation comprises emitting the laser line.

18. The method of claim 12 wherein the step of generating radiation comprises generating radiation comprises emitting radiation having a wavelength range of about 0.94 $\mu$m to about 1.396 $\mu$m.

19. The method of claim 12 wherein the step of providing radiation comprises emitting radiation having a wavelength range of about 0.94 $\mu$m to about 2.7 $\mu$m.

20. The method of claim 12 wherein the step of determining a change in water vapor comprises continually comparing the sensor output to the reference output.

21. An apparatus for detecting a change in water vapor above a cooktop surface, the apparatus comprising:
a radiation source positioned below the cooktop surface for generating and emitting radiation, the emitted radiation having a predetermined water vapor absorption wavelength;
a beam splitter positioned between the cooktop surface and the radiation source for splitting the emitted radiation into at least a first radiation beam and a second radiation beam, the first radiation beam being directed through the cooktop surface to a position above the cooktop surface;
a reflective surface positioned above the cooktop surface for reflecting the first radiation beam toward the cooktop surface;
a radiation sensor positioned below the cooktop surface for detecting the reflected first radiation beam and generating a sensor output corresponding to the reflected radiation beam;
a reference radiation sensor positioned below the cooktop surface for receiving the second radiation beam from the beam splitter and generating a reference output corresponding to the second radiation beam; and
a processor connected to the radiation sensor and the reference radiation sensor, the processor receiving the sensor output and the reference output and determining a change in water vapor above the cooktop surface by analyzing the sensor output and the reference output.

22. The apparatus of claim 21 further comprising a lens positioned below the cooktop surface and proximate to the radiation sensor for focusing the reflected first radiation beam to the radiation sensor.

23. The apparatus of claim 21 further comprising a radiation collector positioned below the cooktop surface and proximate to the radiation sensor for collecting and providing the reflected first radiation beam to the radiation sensor.

24. The apparatus of claim 21 wherein the radiation source comprises an InGaAsP laser.

25. The apparatus of claim 21 wherein the radiation source emits a laser line having a wavelength selected from the group consisting of about 0.94 $\mu$m, about 1.06 $\mu$m, about 1.3 $\mu$m and about 1.396 $\mu$m.

26. The apparatus of claim 21 wherein the radiation source emits radiation having a wavelength range of about 0.94 $\mu$m to about 1.396 $\mu$m.

27. The apparatus of claim 21 wherein the radiation source emits radiation having a wavelength range of about 0.94 $\mu$m to about 2.7 $\mu$m.

28. The apparatus of claim 21 wherein the processor analyzes the sensor output at a predetermined water absorption wavelength of the reflected first radiation beam.

29. The apparatus of claim 28 wherein the predetermined water absorption wavelength is selected from the group consisting of about 0.94 $\mu$m, about 1.1 $\mu$m, about 1.38 $\mu$m, about 1.87 $\mu$m and about 2.7 $\mu$m.

30. The apparatus of claim 21 wherein the radiation source comprises:
a broad-band incoherent light source positioned below the cooktop surface; and
an optical filter positioned proximate to the broad-band incoherent light source for filtering the radiation generated by the broad-band incoherent light source.

31. The apparatus of claim 21 wherein the cooktop surface comprises a glass ceramic.

32. The apparatus of claim 21 wherein the processor analyzes the sensor output and the reference output by continually comparing the sensor output to the reference output.

33. The apparatus of claim 21 wherein the processor is connected to the radiation source.

34. The apparatus of claim 21 wherein the processor is connected to a controller.

35. An apparatus for detecting a change in water vapor above a cooktop surface, the apparatus comprising:

a radiation source positioned below the cooktop surface for generating and emitting radiation, the emitted radiation having a predetermined water vapor absorption wavelength, the radiation source emitting radiation at a predetermined angle to the cooktop surface such that the emitted radiation is split into a first radiation beam and a second radiation beam, the first radiation beam being directed through the cooktop surface to a position above the cooktop surface, the second radiation beam comprising reference radiation;

a reflective surface positioned above the cooktop surface for reflecting the first radiation beam toward the cooktop surface;

a radiation sensor positioned below the cooktop surface for detecting the reflected first radiation beam and generating a sensor output corresponding to the reflected radiation beam;

a reference radiation sensor positioned below the cooktop surface for receiving the second radiation beam and the reference radiation sensor generating a reference output corresponding to the second radiation beam; and a processor connected to the radiation sensor and the reference radiation sensor, the processor receiving the sensor output and the reference output and determining a change in water vapor above the cooktop surface by analyzing the sensor output and the reference output.

36. The apparatus of claim 35 further comprising a lens positioned below the cooktop surface and proximate to the radiation sensor for increasing a field of view of the radiation sensor.

37. The apparatus of claim 35 further comprising a radiation collector positioned below the cooktop surface and proximate to the radiation sensor for increasing a field of view of the radiation sensor.

38. The apparatus of claim 35 wherein the radiation source comprises an InGaAsP laser.

39. The apparatus of claim 35 wherein the radiation source emits a laser line having a wavelength selected from the group consisting of about 0.94 $\mu$m, about 1.06 $\mu$m, about 1.3 $\mu$m and about 1.396 $\mu$m.

40. The apparatus of claim 35 wherein the radiation source emits radiation having a wavelength range of about 0.94 $\mu$m to about 1.396 $\mu$m.

41. The apparatus of claim 35 wherein the radiation source emits radiation having a wavelength range of about 0.94 $\mu$m to about 2.7 $\mu$m.

42. The apparatus of claim 35 wherein the processor analyzes the sensor output at a predetermined water absorption wavelength of the reflected first radiation beam.

43. The apparatus of claim 42 wherein the water absorption wavelength is selected from the group consisting of about 0.94 $\mu$m, about 1.1 $\mu$m, about 1.38 $\mu$m, about 1.87 $\mu$m and about 2.7 $\mu$m.

44. The apparatus of claim 35 wherein the radiation source comprises:

a broad-band incoherent light source positioned below the cooktop surface; and an optical filter positioned proximate to the broad-band incoherent light source for filtering the radiation generated by the broad-band incoherent light source.

45. The apparatus of claim 35 wherein the cooktop surface comprises a glass ceramic.

46. The apparatus of claim 35 wherein the processor analyzes the sensor output and the reference output by continually comparing the sensor output to the reference output.

47. The apparatus of claim 35 wherein the processor is connected to the radiation source.

* * * * *

UNITED STATES PATENT AND TRADEMARK OFFICE
CERTIFICATE OF CORRECTION

PATENT NO.    : 6,417,513 B1
DATED         : July 9, 2002
INVENTOR(S)   : John Erik Hershey et al.

It is certified that error appears in the above-identified patent and that said Letters Patent is hereby corrected as shown below:

<u>Column 9,</u>
Line 64, delete "generating radiation comprises generating radiation comprises" insert therefor -- generating radiation comprises --.

Signed and Sealed this

Thirtieth Day of December, 2003

JAMES E. ROGAN
*Director of the United States Patent and Trademark Office*